US012589176B2

(12) United States Patent
Haller et al.

(10) Patent No.: US 12,589,176 B2
(45) Date of Patent: Mar. 31, 2026

(54) PASSIVE EMISSION FRAGRANCE DIFFUSER FOR PERSONAL USE

(71) Applicant: Scentral Zone, LLC, Edina, MN (US)

(72) Inventors: Christina M. Haller, Minneapolis, MN (US); Rio J. Duran, Chanhassen, MN (US); Ted E. Ahrenholtz, Minnetonka, MN (US)

(73) Assignee: Scentral Zone, LLC, Edina, MN (US)

( * ) Notice: Subject to any disclaimer, the term of this patent is extended or adjusted under 35 U.S.C. 154(b) by 788 days.

(21) Appl. No.: 18/046,722

(22) Filed: Oct. 14, 2022

(65) Prior Publication Data

US 2023/0132890 A1 May 4, 2023

Related U.S. Application Data

(60) Provisional application No. 63/273,596, filed on Oct. 29, 2021.

(51) Int. Cl.
*A61L 9/12* (2006.01)

(52) U.S. Cl.
CPC ........... *A61L 9/12* (2013.01); *A61L 2209/134* (2013.01); *A61L 2209/15* (2013.01)

(58) Field of Classification Search
None
See application file for complete search history.

(56) References Cited

U.S. PATENT DOCUMENTS 1,307,359 A 6/1919 Hugetz
1,839,073 A 12/1931 Wright 2,609,230 A 9/1952 Raleigh
2,763,395 A 9/1956 Meek
3,480,370 A 11/1969 Koeln
3,525,573 A 8/1970 Fend
3,583,820 A 6/1971 Koeln
3,594,091 A 7/1971 Bleuer
(Continued)

FOREIGN PATENT DOCUMENTS

CN 2212329 11/1995
CN 2733954 Y 10/2005
(Continued)

OTHER PUBLICATIONS

European Patent Office, Extended European Search Report (R. 62 EPC), counterpart European Patent Application No. 122204580.9 (Mar. 17, 2023).

*Primary Examiner* — Jelitza M Perez
(74) *Attorney, Agent, or Firm* — Schroeder & Siegfried, P.A.

(57) ABSTRACT

A passive emission fragrance delivery mechanism/diffuser assembly which includes an outer tubular housing body that carries an inner movable piston and fragrance carrier/diffusion member for selectively dispensing a non-spray fragrant emission upon axial movement of the piston within the tubular housing. The fragrance diffusion member includes a scent-impregnated material which may be movable with the piston or stationery relative thereto within the outer body. The piston is longer than the outer tubular body, so as to always extend beyond the confines of the outer body through one of its open ends. The piston is constructed with an interference fit with the housing body so as to seal the fragrance carrier member therein when not in use.

20 Claims, 14 Drawing Sheets

(56) References Cited

U.S. PATENT DOCUMENTS

| | | | |
|---|---|---|---|
| 3,679,133 | A | 7/1972 | Sekiguchi et al. |
| 3,733,016 | A | 5/1973 | Rood |
| D228,911 | S | 10/1973 | Gatter |
| 3,770,199 | A | 11/1973 | Hoek et al. |
| 3,888,416 | A | 6/1975 | Lin |
| 3,951,622 | A | 4/1976 | Wilk |
| 4,055,672 | A | 10/1977 | Hirsch et al. |
| 4,145,001 | A | 3/1979 | Weyenberg et al. |
| 4,157,787 | A | 6/1979 | Schwartz |
| 4,161,284 | A | 7/1979 | Rattan |
| 4,165,835 | A | 8/1979 | Dearling |
| 4,173,604 | A | 11/1979 | Dimacopoulos |
| 4,244,525 | A | 1/1981 | Manna |
| 4,251,032 | A | 2/1981 | Werding |
| 4,269,525 | A | 5/1981 | Melikian |
| 4,356,969 | A | 11/1982 | Obermayer et al. |
| D268,695 | S | 4/1983 | Kolf |
| 4,445,641 | A | 5/1984 | Baker et al. |
| 4,452,052 | A | 6/1984 | Hodge |
| 4,523,870 | A | 6/1985 | Spector |
| 4,540,300 | A | 9/1985 | Midorikawa |
| 4,711,592 | A | 12/1987 | Gregory |
| 4,728,212 | A | 3/1988 | Spector |
| 4,759,650 | A | 7/1988 | Granoff |
| 4,762,275 | A | 8/1988 | Herbert et al. |
| 4,788,787 | A | 12/1988 | Konietzki |
| 4,793,555 | A | 12/1988 | Lee et al. |
| 4,809,912 | A | 3/1989 | Santini |
| D301,912 | S | 6/1989 | Ward |
| 4,866,952 | A | 9/1989 | Hight et al. |
| 4,889,285 | A | 12/1989 | Locko |
| 4,898,328 | A | 2/1990 | Fox et al. |
| 4,913,349 | A | 4/1990 | Locko |
| 4,979,673 | A | 12/1990 | Wilk |
| 5,000,383 | A | 3/1991 | van der Heijden |
| 5,048,990 | A | 9/1991 | Hashimoto et al. |
| 5,174,814 | A | 12/1992 | Burwell et al. |
| 5,230,867 | A | 7/1993 | Kunze et al. |
| 5,332,325 | A | 7/1994 | Crosnier et al. |
| 5,348,031 | A | 9/1994 | Cloud |
| 5,478,505 | A | 12/1995 | McElfresh et al. |
| 5,527,493 | A | 6/1996 | McElfresh et al. |
| 5,544,812 | A | 8/1996 | Torres |
| 5,611,165 | A | 3/1997 | Blaha |
| 5,716,000 | A | 2/1998 | Fox |
| 5,746,019 | A | 5/1998 | Fisher |
| 5,752,658 | A | 5/1998 | Gibbs et al. |
| 5,765,751 | A | 6/1998 | Joshi |
| 5,832,648 | A | 11/1998 | Malone |
| 5,865,372 | A | 2/1999 | Ceresko |
| 5,885,701 | A | 3/1999 | Berman et al. |
| 5,906,298 | A | 5/1999 | Ward |
| 5,947,621 | A * | 9/1999 | Szekely ............. A45D 40/16 |
| | | | 401/175 |
| 6,126,040 | A | 10/2000 | Hippensteel |
| 6,135,431 | A | 10/2000 | Muhmel et al. |
| 6,241,161 | B1 | 6/2001 | Corbett |
| 6,264,887 | B1 | 7/2001 | Farmer |
| 6,328,287 | B2 | 12/2001 | Wittek |
| 6,481,639 | B1 | 11/2002 | Pozzo |
| 6,578,726 | B1 | 6/2003 | Schaefer |
| 6,615,881 | B2 | 9/2003 | Bartholomew et al. |
| 6,648,239 | B1 | 11/2003 | Myny et al. |
| 6,745,950 | B1 | 6/2004 | Longo |
| 6,857,579 | B2 | 2/2005 | Harris |
| 6,899,486 | B2 | 5/2005 | Wetzel et al. |
| 6,929,119 | B2 | 8/2005 | Shaki |
| 7,046,919 | B2 | 5/2006 | Shimizu et al. |
| 7,070,172 | B2 | 7/2006 | Fabrega et al. |
| 7,093,773 | B2 | 8/2006 | Kuiper |
| 7,147,171 | B2 | 12/2006 | Harada et al. |
| 7,182,270 | B2 | 2/2007 | Buthier |
| 7,188,783 | B2 | 3/2007 | Ivey et al. |
| 7,273,184 | B2 | 9/2007 | Brown et al. |
| 7,293,719 | B2 | 11/2007 | Wheatley et al. |
| 7,437,061 | B2 | 10/2008 | Manne |
| 7,481,380 | B2 | 1/2009 | Kvietok et al. |
| 7,488,130 | B2 | 2/2009 | Dylkiewicz et al. |
| 7,651,009 | B2 | 1/2010 | Grant |
| 7,687,038 | B2 | 3/2010 | Wheatley et al. |
| 7,775,734 | B2 | 8/2010 | Dylkiewicz et al. |
| 7,877,118 | B2 | 1/2011 | Park |
| 7,988,073 | B2 | 8/2011 | Ligny et al. |
| 8,016,165 | B2 | 9/2011 | Margheritis et al. |
| D648,430 | S | 11/2011 | Short et al. |
| 8,052,934 | B2 | 11/2011 | Manne |
| 8,074,640 | B2 | 12/2011 | Davies et al. |
| 8,221,012 | B2 | 7/2012 | Rennecker |
| 8,226,312 | B2 | 7/2012 | Rennecker et al. |
| 8,261,946 | B2 | 9/2012 | Grant |
| 8,336,583 | B2 | 12/2012 | Jacobs et al. |
| 8,480,960 | B2 | 7/2013 | Wheatley et al. |
| 8,870,165 | B2 | 10/2014 | Scolari |
| 8,893,985 | B2 | 11/2014 | Wu |
| 8,950,632 | B2 | 2/2015 | Ciavarella et al. |
| 8,978,998 | B1 | 3/2015 | Talley |
| 9,028,348 | B2 | 5/2015 | Lazenby |
| 9,060,506 | B2 | 6/2015 | Broderick |
| 9,107,969 | B2 | 8/2015 | Lesniak et al. |
| 9,234,338 | B2 | 1/2016 | Irwin et al. |
| 9,258,988 | B2 | 2/2016 | Willenberg et al. |
| 9,320,288 | B2 | 4/2016 | Wood et al. |
| D761,408 | S | 7/2016 | Kramer et al. |
| 9,393,335 | B2 | 7/2016 | Santini et al. |
| D768,836 | S | 10/2016 | Van Der Starre |
| 9,521,836 | B2 | 12/2016 | Willert et al. |
| 9,526,809 | B2 | 12/2016 | Pizzini |
| D777,576 | S | 1/2017 | Peng |
| 9,586,719 | B2 | 3/2017 | Hafer et al. |
| 9,669,012 | B2 | 6/2017 | Anderson et al. |
| 9,694,096 | B2 | 7/2017 | McKay et al. |
| 9,731,042 | B2 | 8/2017 | Seavone et al. |
| 9,849,206 | B1 | 12/2017 | Hsiao |
| 9,925,550 | B2 | 3/2018 | Dring et al. |
| 9,931,425 | B2 | 4/2018 | Edwards et al. |
| 9,994,066 | B2 | 6/2018 | Hayao et al. |
| 10,098,384 | B2 | 10/2018 | Wu |
| 10,098,978 | B2 | 10/2018 | Saleh et al. |
| 10,105,462 | B2 | 10/2018 | Joshi |
| 10,124,082 | B2 | 11/2018 | Santini et al. |
| 10,143,766 | B2 | 12/2018 | Gruenbacher et al. |
| 10,188,094 | B2 | 1/2019 | Wynalda, Jr. |
| 10,213,519 | B2 | 2/2019 | Seshadri et al. |
| 10,245,877 | B2 | 4/2019 | Debartolo, Jr. et al. |
| 10,258,708 | B2 | 4/2019 | D'Amico |
| 10,278,382 | B2 | 5/2019 | Wynalda, Jr. |
| 10,327,444 | B2 | 6/2019 | Topchik |
| 10,342,315 | B2 | 7/2019 | Maehr |
| 10,362,853 | B2 | 7/2019 | Seidler |
| 10,391,191 | B2 | 8/2019 | Cutler et al. |
| 2002/0109013 | A1 | 8/2002 | Desrosiers |
| 2004/0050950 | A1 | 3/2004 | Brown |
| 2005/0220664 | A1 | 10/2005 | Hitzler et al. |
| 2006/0067859 | A1 | 3/2006 | Laudamiel-Pellet et al. |
| 2006/0126444 | A1 | 6/2006 | Ellner et al. |
| 2010/0102142 | A1 | 4/2010 | Tagliareni |
| 2010/0181319 | A1 | 7/2010 | Deflorian et al. |
| 2011/0146133 | A1 | 6/2011 | Bunker et al. |
| 2011/0192912 | A1 | 8/2011 | Herd et al. |
| 2012/0110888 | A1 | 5/2012 | Hatridge et al. |
| 2014/0021225 | A1 | 1/2014 | Francavilla |
| 2015/0014428 | A1 | 1/2015 | Rome |
| 2016/0174694 | A1 | 6/2016 | Metzger et al. |
| 2017/0122708 | A1 | 5/2017 | Gorinas et al. |
| 2017/0216519 | A1 | 8/2017 | Vouillamoz et al. |
| 2017/0231338 | A1 | 8/2017 | Thomas |
| 2018/0071425 | A1 | 3/2018 | Jin et al. |
| 2019/0289979 | A1 | 9/2019 | Groffsky et al. |

FOREIGN PATENT DOCUMENTS

| | | |
|---|---|---|
| CN | 104323538 | 2/2015 |
| DE | 19635528 A1 | 2/1997 |
| DE | 19715404 | 2/1998 |

(56)     References Cited

FOREIGN PATENT DOCUMENTS

| | | | |
|---|---|---|---|
| DE | 19710754 | A1 | 9/1998 |
| DE | 19724953 | A1 | 9/1998 |
| DE | 202006009161 | U1 | 10/2006 |
| DE | 202017105260 | U1 | 10/2017 |
| DK | 167853 | B1 | 12/1993 |
| EP | 0218891 | | 4/1987 |
| EP | 0218892 | | 4/1987 |
| EP | 0442793 | A1 | 8/1991 |
| EP | 1932545 | A1 | 6/2008 |
| GB | 2251601 | | 7/1992 |
| GB | 2373430 | | 9/2002 |
| JP | 2014500095 | A | 1/2014 |
| KR | 20030037396 | A | 9/2004 |
| KR | 200436510 | Y1 | 8/2007 |
| KR | 200436761 | Y1 | 10/2007 |
| KR | 200458804 | Y1 | 3/2012 |
| KR | 20130126176 | A | 11/2013 |
| KR | 20140054504 | A | 5/2014 |
| KR | 20190001258 | U | 5/2019 |
| WO | 2008108769 | | 9/2008 |
| WO | 2009054597 | | 4/2009 |
| WO | WO-2009054597 A1 * | | 4/2009 .............. A61L 9/12 |
| WO | 2013106982 | | 7/2013 |

* cited by examiner

PASSIVE EMISSION FRAGRANCE DIFFUSER FOR PERSONAL USE

CROSS REFERENCE TO RELATED APPLICATIONS

This application is a nonprovisional patent application which claims the benefit of U.S. Provisional Application Ser. No. 63/273,596, filed on Oct. 29, 2021, entitled "Non-spray Passive Fragrance Diffuser For Personal Use," the contents of which is incorporated herein in its entirety by reference thereto.

FIELD OF INVENTION

The present invention relates generally to the art of passive fragrance diffusers, and more specifically to a non-spray passive emission fragrance diffuser with a unique simplified push activation mechanism for transitioning a fragrance carrier member between a sealed storage position and an aromatic position open to the surrounding airspace.

BACKGROUND

The statements in this section merely provide background information related to the present disclosure and may not constitute prior art.

Perfumes and fragrance dispensers of many kinds have historically been used to help mask or eliminate odors. Fragrance diffusers in the nature of wicking devices, ultrasonic aroma diffusers, air-vent clips, aerosol sprays, charcoal bags, scented candles and scent-emitting jewelry/rings, etc., are just some of the many devices that have been used for this purpose, and more. Indeed, adding a pleasant aroma to the surrounding environment has also been considered helpful in boosting one's self-confidence and body image, and enhancing mood, attractiveness, and health. Aromatherapy is often used in treatments for insomnia and headaches, and has long been widely considered an effective aphrodisiac.

The difficulty with many of the conventional fragrance diffuser devices, however, is that they are not designed to facilitate or allow for wide versatility and flexibility in use. Many of such aforementioned devices are designed for in-house mounting or stationary use only, i.e., to be set on a table; plugged into a wall socket; or clipped onto an air-vent (such as in a car). Many of these devices are unsightly, relatively large and/or just take up otherwise usable space and are prone to being knocked over and spilled.

Other aerosol and spray-type fragrance devices are also available, but these devices require an operator to specifically spray those areas for which an aroma is desired and require periodic reuse of the device to avoid the aerosol from dissipating into the surrounding environment. Such devices are not normally long-lasting, require frequent user interaction, and can be annoying to those in immediate surrounding areas. Even fragrance devices which are designed for more personal use as a jewelry pendant, finger-ring or the like are generally complicated in design and difficult to easily activate and deactivate, when desired. Such devices are generally not very user-friendly and are designed more as a decorative piece which has limited functionality in other environments.

It is evident, therefore, that there is a distinct need for an improved long-lasting passive fragrance diffuser which is compact in size and highly versatile for personal use in a multiplicity of circumstances and different environments, and which is simple in design to facilitate easy activation and deactivation, as desired. It is with these objectives in mind, and more, that we have developed our improved passive, non-spray fragrance diffuser, as will be described in more detail below.

SUMMARY

In furtherance of the foregoing objectives, the present invention is comprised of a new non-spray passive fragrance delivery mechanism/diffuser assembly which includes an outer tubular housing body which carries an inner movable piston and fragrance diffusion member for selectively dispensing a fragrance to ambient air outside the tubular housing upon axial movement of the piston within the tubular housing. More specifically, the inner movable piston is constructed to carry a fragrance carrier member, such as a section of silicone or other absorptive material impregnated with a fragrant oil. The piston is longer than the outer tubular body, so it always extends beyond the confines of the body through one of the open ends thereof. The piston is constructed with an interference fit with the housing body so as to seal the fragrance carrier member therein when not in use.

Upon pushing the piston in one axial direction, outlet passages formed in one exposed end of the piston permit the scent from the fragrance carrier to escape into the surrounding environment. Upon pushing the piston axially in the other direction, the piston seals against the outer housing body and prevents the fragrance of the carrier member from being dispersed into the surrounding environment.

The simplicity of this design permits the device to be constructed in small compass as an accessory piece which may be clipped to any piece of clothing or other personal article, such as a handbags, gym bags, and the like. Optionally, the fragrance diffuser assembly may also be designed either as a long-lasting throw-away device or as a device which is refillable by the user with any desired fragrance or essential oil.

The foregoing and additional features and advantages of the present invention will be more readily apparent from the following detailed description. It should be understood, however, that the description and specific examples herein are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1A:
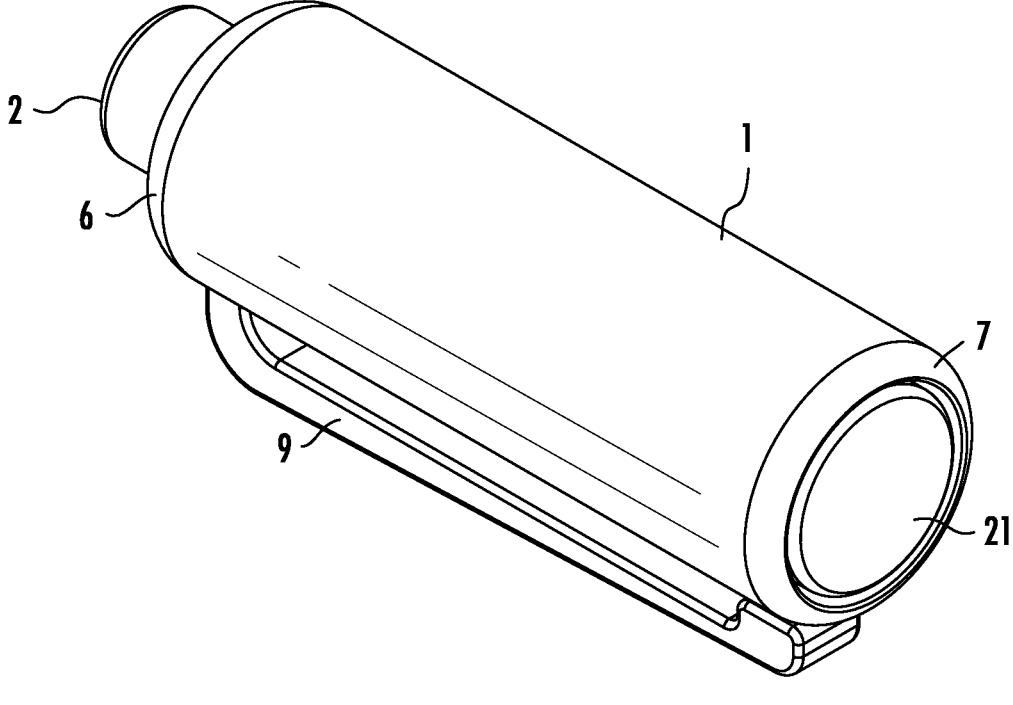
FIG. 1A is a perspective view of our new passive emission fragrance diffuser, showing the diffuser in its assembled closed position.

The following description is merely exemplary in nature and is not intended to limit the present disclosure, application, or uses. It should be understood that throughout the drawings, corresponding reference numerals indicate like or corresponding parts and features.

With reference now to FIGS. 1A-1E of the drawings (hereinafter collectively "FIG. 1"), an exemplary embodiment is shown of our new non-spray passive fragrance delivery mechanism/diffuser in its assembled state. The diffuser assembly is comprised generally of an outer tubular body member 1 with an inner telescopically slidable piston 2 which incorporates a fragrance carrier/diffusion member 3. The outer tubular body member 1 has openings 4 and 5 within its opposite ends 6 and 7, respectively, which communicate with a central body chamber 8 where the slidable piston 2 is carried.

As shown in FIG. 1, the piston 2 is longer than the outer tubular body 1 such that it always protrudes through at least one of the end openings 4 or 5 thereof, depending on how the slidable piston 2 is positioned within the outer body 1. With this design, the inner piston 2 may be manually pushed in one direction (FIGS. 1B & 1C) to activate/open the fragrance diffuser and permit fragrance to passively disperse into the surrounding environment, or be pushed in the opposite direction (FIGS. 1D-1E) to deactivate/close the fragrance diffuser as a sealed, contained unit. A friction fit of the piston 2 to the outer tubular body 1 adjacent ends 6 and 7 thereof prevents leakage of the fragrance when not in use. The simplicity of this design permits the device to be constructed in small compass as an accessory piece which may be clipped via an attachment member 9 to any piece of clothing or other personal article.

For the aforementioned sealing to occur between the outer tubular body 1 and inner piston 2, it is contemplated that the outer tubular body 1 of the diffuser be formed of a relatively rigid material, such as stainless steel, aluminum or other suitably rigid metal or plastic material. In due part, the inner piston 2, or at least the sealing portions thereof, should be formed of a material having some capacity for conformance to be capable of providing the required sealing function against the outer body member 1. Such materials may include, without limitation, Linear Low-Density Polyethylene (LLPE), Low Density Polyethylene (LPE), Perfluoroalkoxy alkanes (PFA), High Density Polyethylene (HDPE), Urethanes, Thermoplastic Urethanes (TPU) and rubber materials. Other suitable known sealing materials are also readily available.

Figures 1B, 1C:
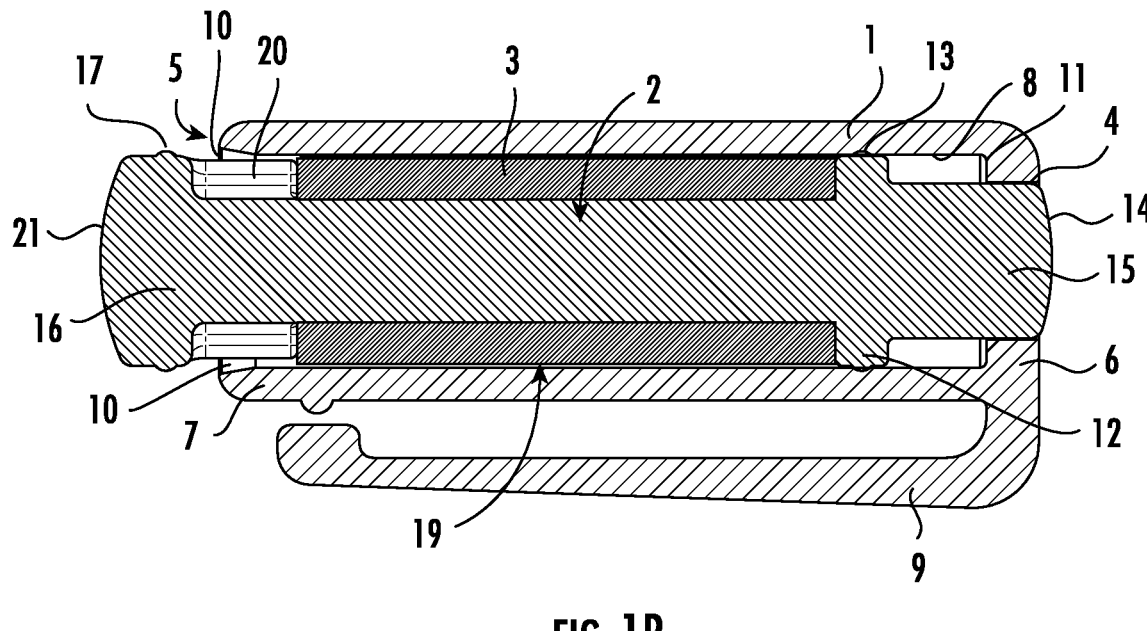
FIG. 1B is a vertical cross section view of the fragrance diffuser shown in FIG. 1A, shown in its open position.
FIG. 1C is a side elevation view of the fragrance diffuser shown in FIG. 1A, show in its open position.
Figure 1D:
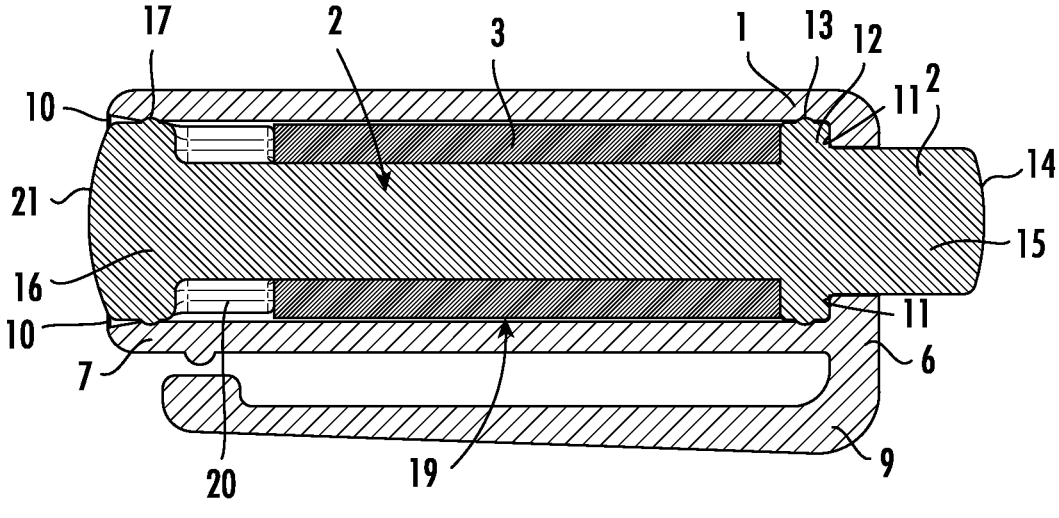
FIG. 1D is a vertical cross-section view of the fragrance diffuser shown in FIG. 1A, shown in its closed position.

Referring further to FIGS. 1B and 1D of the drawings, it can be seen that the terminal end 7 of the outer tubular member 1 has a slight outward radial taper 10 at opening 5. As best seen in FIG. 1D, this taper 10 functions as a piston guide against which the inner piston 2 will bear to be guided into proper sealed relation with body 1 when the fragrance diffuser is deactivated and closed. It is contemplated that taper 10 may be approximately ten degrees (10°) relative to the inner surface of chamber 8 of body 1, adjacent end 7. However, it is certainly possible that other taper angles may also be sufficient for the stated purpose without departing from the invention herein.

At the opposite end 6 of the body member 1, a radially inward protruding annular terminal shoulder 11 is formed which diametrically constricts the end opening 4 relative to the interior dimensions of chamber 8. As will be discussed hereafter, shoulder 11 creates a stop for piston 2 within chamber 8. This helps to facilitate proper sealed positioning of piston 2 when the fragrance diffuser is closed, and also prevents potential damage of piston 2 as a result of overtravel within body member 1.

Figure 3A:
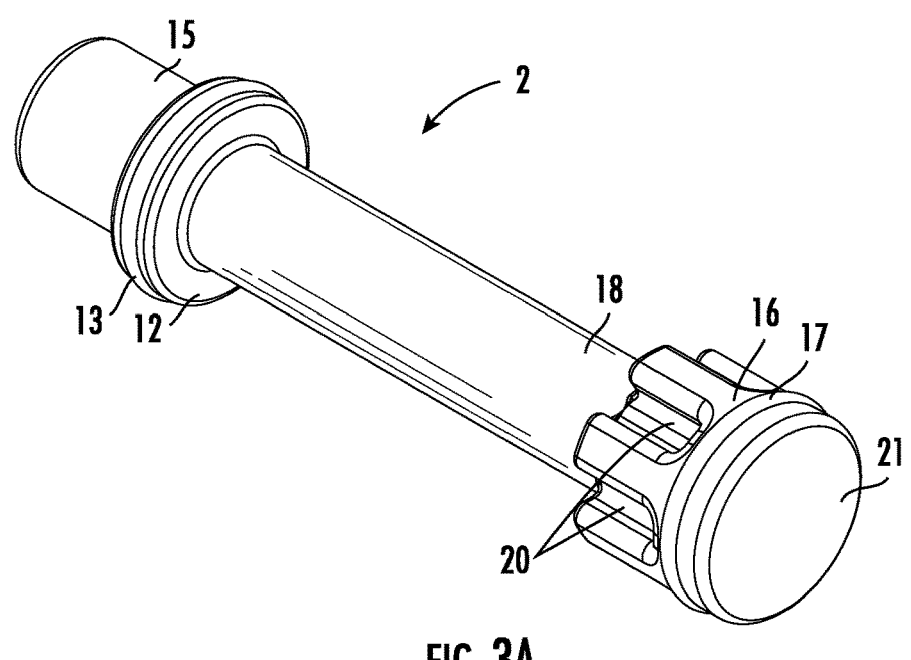
FIG. 3A is a perspective view of the inner piston member which is received within the outer tubular body of the fragrance diffuser shown in FIG. 1A.
Figure 3B:
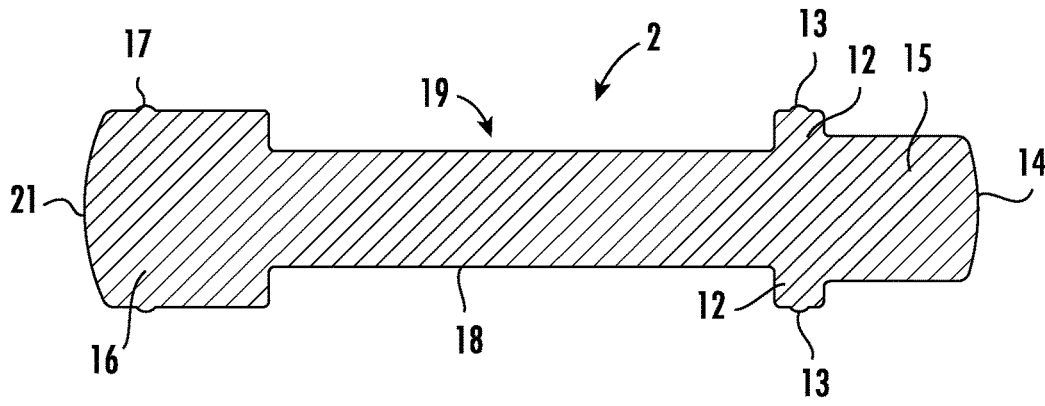
FIG. 3B is a vertical cross-section view of the inner piston member shown in FIG. 3A.
Figure 3C:
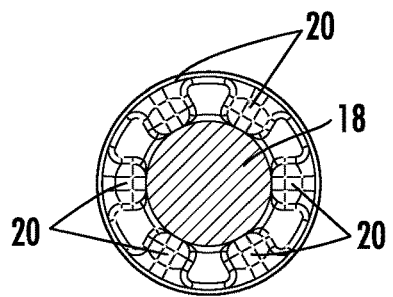
FIG. 3C is an end view of the piston member shown in FIG. 3A, taken from the left side thereof as shown in the drawing.

With reference now being had to FIGS. 3A-3C of the drawings (hereinafter collectively "FIG. 3"), the construction of piston 2 is shown in greater detail. As seen, piston 2 is an elongated member having opposite end portions 15 and 16. Notably, for most effective and efficient operation of the present fragrance diffuser, it is contemplated that piston 2 be greater in length than the outer tubular body 1 within which it is carried. If so, as best seen in FIG. 1, at least one of the end portions 15 and 16 of the slidable piston 2 will be visibly exposed and readily accessible at all times to the user. Thus, the user may easily activate and deactivate the fragrance diffuser, and adjust the positioning of piston 2 within the tubular outer body 1, by merely pushing the piston 2 in one direction or the other with one's fingers.

Figure 1E:
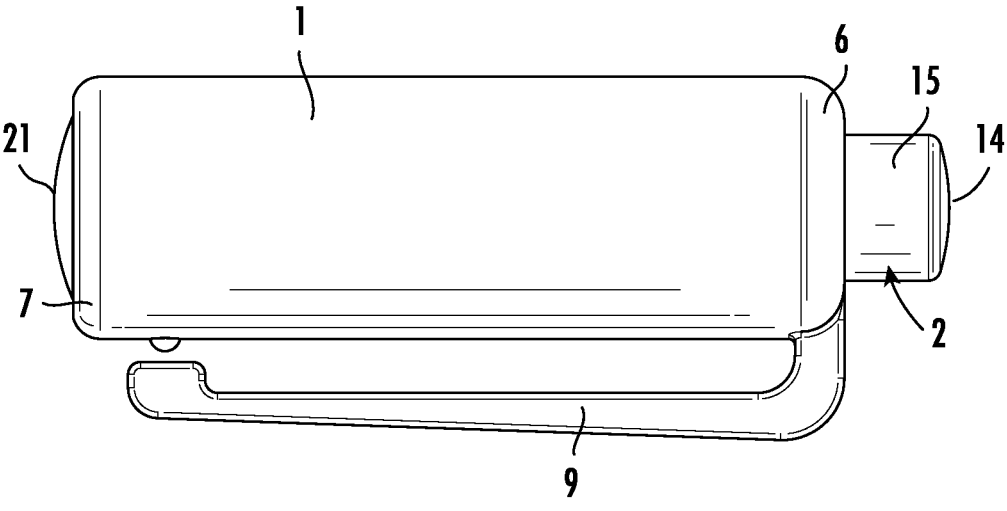
FIG. 1E is a side elevation view of the fragrance diffuser shown in FIG. 1A, shown in its closed position.
Figure 2A:
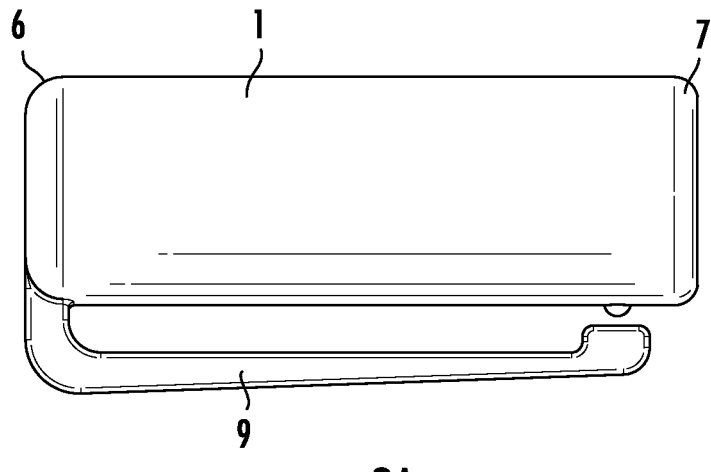
FIG. 2A is a side elevation view of the outer tubular body of the fragrance diffuser shown in FIG. 1A.
Figure 2B:
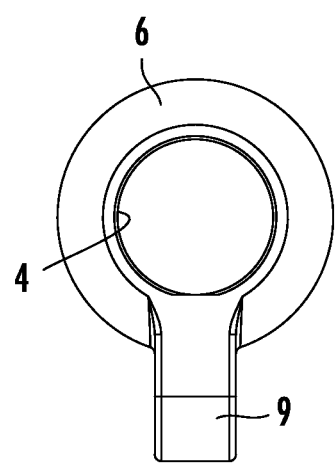
FIG. 2B is an end view of the tubular body shown in FIG. 2A, viewed from the left side thereof in the drawing.

To explain further, in the embodiment shown in FIGS. 1-3, it can be seen that end portion 15 of piston 2 is constructed with a cross-sectional shape and dimensions closely approximating, but slightly less than, that of opening 4 in the outer tubular body member 1. Accordingly, end portion 15 of piston 2, which is aligned with opening 4 in tubular body member 1, is permitted to move freely through opening 4 of body 1 upon axial pressure being applied to one of the opposite end portions 15 or 16 of piston 2. As further shown, the opposite end portion 16 of piston 2 is compliantly sized to slide in and out of the opening 5 formed in the opposite end 7 of the outer body 1. The cross-sectional or diametrical dimensions of end portion 16 of piston 2 are sized just slightly less than that of the inner wall surface of chamber 8 of body 1, such that end portion 16 of piston 2 is permitted to move freely through opening 5 of body 1 upon axial pressure being applied to one of the opposite end portions 15 or 16 of piston 2.

As further shown in FIGS. 1 and 3, to perfect a seal of piston 2 against the inner wall surface of chamber 8 and control movement thereof within the outer body 1, piston 2 is formed adjacent one end with a radially outward protruding piston ring 12. Although piston ring 12 is shown as being preferably molded integrally and homogenously with the remainder of the piston 2, it is contemplated that it may be formed as a separately engineered component without departing from the invention herein. In the present embodiment, piston ring 12 is located axially inward from the distal end 14 of piston 2 and is correspondingly sized to seal circumferentially against the interior wall surface of chamber 8. As shown, piston ring 12 includes at least one annular lobe 13 extending about its periphery which functions to bear against the interior wall surface of chamber 8 and help effect a proper seal thereagainst.

The opposite end portion 16 of piston 2 is also constructed with at least one annular sealing lobe 17 extending about its periphery. As best shown in FIG. 1D, upon closure of the fragrance diffuser, end portion 16 of piston 2 is guided within opening 5 of tubular body 1 by the tapered edge 10 thereof. Once seated, sealing lobe 17 bears firmly in sealing relation against the inner wall surface of chamber 8 of body 1, and thus seals the opposite end 16 of the fragrance diffuser. Consequently, by pressing the end portion 16 of piston 2 axially inward within the confines of the outer body 1, both end portions 15 and 16 of piston 2 are caused to seal against the inner wall surface of chamber 8, thus sealing the entire intermediate section 18 of piston 2 from exposure to the ambient air or outer atmosphere of the surrounding environment.

As best shown in FIGS. 1 and 3, the intermediate section 18 of piston 2 is smaller in diameter than the adjoining end portions 15 and 16 thereof. Intermediate section 18 is adapted to carry the fragrance carrier member 3 (see FIGS. 1B & 1D), which is tubular in configuration. Fragrance carrier member 3 can be constructed of any material capable of absorbing and passively emitting the fragrance of an essential oil or other scented oil/liquid with which it is impregnated. Such known materials may include, without limitation, silicone, cotton, paper, wood, stone, ceramic, etc., or combinations thereof.

As seen best in FIG. 1, the fragrance carrier member 3 preferably has an interior diameter which corresponds to the outer diameter of the intermediate section 18, and an outer diameter which is adapted to be telescopically received in slidable relation within the inner confines of the body member 1. In fact, as shown in FIGS. 1B & 1D, the fragrance carrier 3 is constructed with an outside diameter which is just slightly less than the inside diameter of chamber 8 of the body member 1. This creates a minor clearance between fragrance carrier 3 and tube 1 which accommodates for possible swelling of the fragrance carrier 3 when impregnated with a scent oil. Therefore, fragrance carrier 3 is designed to slide freely with piston 2 inside of tubular body 1 at all times without any significant interference with the inner wall of tubular member 1.

Accordingly, the fragrance carrier member 3 is contained in an area 19 extending radially between the intermediate section 18 of piston 2 and the inner wall surface of chamber 8 of outer body member 1. Axially, the fragrance carrier member 3 is held in place by end portion 16 and piston ring 12 of piston 2. As such, the fragrance carrier member 3 is retained in the area 19 between opposing sealing lobes 13 and 17 formed in piston ring 12 and end portion 16, respectively. Thus, when the fragrance diffuser is closed, the fragrance carrier member 3 is sealed atmospherically inside body member 1 from the outside environment.

As shown best in FIG. 3, axially inward from sealing lobe 17 and at the juncture between end portion 16 and intermediate section 18 of piston 2, at least a portion of the circumference of end portion 16 is fluted with a plurality of axially extending open channels 20 which extend toward the open area 19 that surrounds the intermediate section 18 of piston 2. As seen best in FIG. 1, when the fragrance diffuser is assembled, these channels 20 fluidly communicate with the open area 19 within which the fragrance carrier member 3 is contained and carried by the intermediate section 18 of piston 2.

Accordingly, from a closed, deactivated position (FIG. 1E), activating the fragrance diffuser may be accomplished by simply applying inward axial pressure upon end 14 of piston 2 thus causing piston 2 to slide axially within outer body 1. Such movement has the effect of breaking the seal between end portion 16 of piston 2 and the outer tubular body 1. When such seal is broken, the fragrance from the fragrance diffuser is permitted to flow from the contained space 19 within outer body 1, through channels 20 formed in end portion 16 of piston 2, and out to the surrounding atmosphere. Depending on how far inward end portion 15 of piston 2 is moved dictates how much of the axially extending channels 20 will be exposed to the atmosphere, and consequently how much fragrance is emitted to the surrounding environment. Thus, the amount and strength of the scent emitted by the fragrance diffuser may be effectively controlled through adjustment of the positioning of piston 2 within the outer body 1. When the end 14 of piston 2 is pressed axially inward to a position substantially flush with the end 6 of outer body 1 (FIG. 1C), the fragrance diffuser is constructed to be near or fully open with channels 20 having maximum exposure to the surrounding atmosphere.

The fluted section of end portion 16 with channels 20 also creates a barrier between the fragrance carrier material 3 and the outside environment. Therefore, there is no direct contact between the fragrance carrier material 3 and the skin/clothing of the person wearing the fragrance diffuser, or other article to which the fragrance diffuser is clipped. One can safely open and close the diffuser without concern of coming in direct contact with the fragrant oil. This allows the fragrance diffuser to be clipped virtually anywhere desired, either visibly on the exterior of a clothing article or on the inside, out of sight. By securing the fragrance diffuser to the inside on a person's clothing article, the body temperature of an individual can actually help heat the silicone/material of the fragrance carrier 3 and increase emission/evaporation of the scented oil, thus enhancing the release of fragrance.

It is noteworthy that the foregoing discussion describes the fragrance carrier member 3 as being carried by the piston 2 in movable relation to the outer body 1 of the fragrance diffuser. However, it is certainly conceivable that the fragrance carrier member 3 could be retained by the outer body member 1 in a stationary position relative to the sliding tubular member 2, without departing from the scope of the invention herein. In either case, movement of the slidable piston 2 in one direction or the other will effectively open or close the sealed ends of the diffuser, thereby allowing emission of the fragrance through channels 20 to the surrounding atmosphere or sealing the same therefrom.

The fragrance carrier material 3 can be either pre-scented and used as a throwaway item, if desired, or it is contemplated that additional fragrant oil can be added to the fragrance carrier material 3 through the vented channel openings 20 formed on the end 16 of piston 2. It may also be possible to form the fragrance carrier 3 as a replaceable item, such that the fragrance diffuser is reusable. Still further, the fragrance carrier 3 could be sold separately from the fragrance oil, thus allowing the user to self-infuse the fragrance carrier 3 prior to use with any of a variety of different fragrance oils, as desired.

To close and deactivate the fragrance diffuser, axial pressure may simply be applied to end 21 of piston 2, thus causing movement of piston 2 from its open position shown in FIG. 1C toward its closed position shown in FIG. 1E. As piston 2 progresses in this direction, channels 20 formed in end portion 16 of piston 2 become less exposed to the surrounding environment, and the fragrance begins to dissipate. Upon reaching full closure, as shown in FIG. 1E, both seal 13 on piston ring 12 and seal 17 on end portion 16 of piston 2 are perfected, thus closing off all fragrance from the surrounding environment.

As is evident from the drawings, the location of piston ring 12 upon piston 2 is instrumental in ensuring proper function and effective sealing of the fragrance diffuser upon closure. As seen best in FIGS. 1B & 1D, piston ring 12 is diametrically larger than the opening 4 in the outer body 1 of the fragrance diffuser. As shown, outer body 1 is formed at its end 6 with an inward protruding shoulder 11 which creates a travel-stop for piston ring 12. As piston ring 12 approaches end 6 of the outer body 1, it catches on shoulder 11 and is restricted from passing thereby. Shoulder 11 thus stops axial movement of piston ring 12, and consequently piston 2, precisely at the appropriate position to effect a proper seal against outer tubular body 1. Additionally, restriction of movement of piston 2 by shoulder 11 helps prevent possible over-travel of piston 2 within body 1, and consequent damage thereto. Accordingly, the location of piston ring 12 is determined and preset by design such that, upon closure of the fragrance diffuser (FIG. 1E), both end portions 15 and 16 of piston 2 are sealed against the out tubular body 1 and over-travel of the piston 2 is prevented. This prevents the fragrance carrier member 3 contained within body 1 from emitting any gases into the surrounding environment upon closure of the device.

With reference now to FIGS. 4A-4G of the drawings (hereinafter collectively "FIG. 4"), an alternative embodiment of our new non-spray passive fragrance diffuser assembly is disclosed. The diffuser assembly 100 shown in the present embodiment is comprised of a generally rectangular or oval-shaped outer tubular body member 101 with inner telescopically slidable piston 102 which incorporates a fragrance carrier/diffusion member 103. Similar to the embodiment of FIGS. 1-3, the outer tubular body member 101 has openings 104 and 105 formed in its opposite ends 106 and 107, respectively, which communicate with a central body chamber 108 where the slidable piston 102 is carried.

As shown in FIG. 4, the piston 102 is longer than the outer tubular body 101 such that it always protrudes through at least one of the end openings 104 or 105 thereof, depending on how the slidable piston 102 is positioned within the outer body 101. With this design, the inner piston 102 may be manually pushed in one direction (as shown in FIGS. 4C & 4D) to activate/open the fragrance diffuser and permit fragrance to passively disperse into the surrounding environment. As shown in FIG. 4G and described in further detail hereafter, pushing piston 102 in the opposite direction will cause the diffuser 100 to close as a sealed, contained unit. A friction fit of the piston 102 to the outer tubular body 101 adjacent ends 106 and 107 thereof prevents leakage of the fragrance when not in use. The simplicity of this design permits the device to be constructed in small compass as an accessory piece which may be clipped via an attachment member 109 to any piece of clothing or other personal article.

Similar to the previous embodiment, for sealing to occur between the outer tubular body 101 and inner piston 102, the outer tubular body 101 of the diffuser 100 is formed of a relatively rigid material, such as stainless steel, aluminum or other suitably rigid metal or plastic material. In due part, the inner piston 102, or at least the sealing portions thereof, should be formed of a material having some capacity for conformance to be capable of providing the required sealing function against the outer body member 101. As previously discussed, such materials may include, without limitation, Linear Low Density Polyethylene (LLPE), Low Density Polyethylene (LPE), Perfluoroalkoxy alkanes (PFA), High Density Polyethylene (HDPE), Urethanes, Thermoplastic Urethanes (TPU) and rubber materials. Other suitable known sealing materials are also readily available.

Figure 5A:
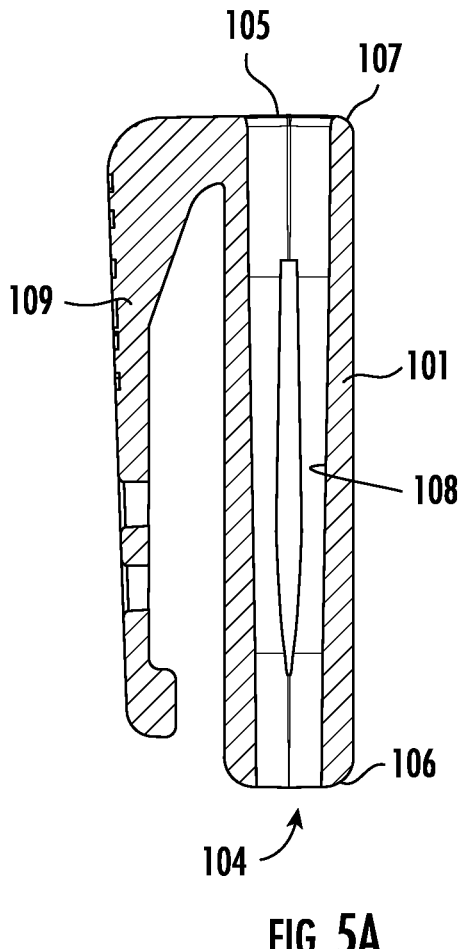
FIG. 5A is a vertical section of the outer tubular body of the fragrance diffuser shown in FIG. 4A, viewed from the left side thereof as shown in the drawing.
Figure 5B:
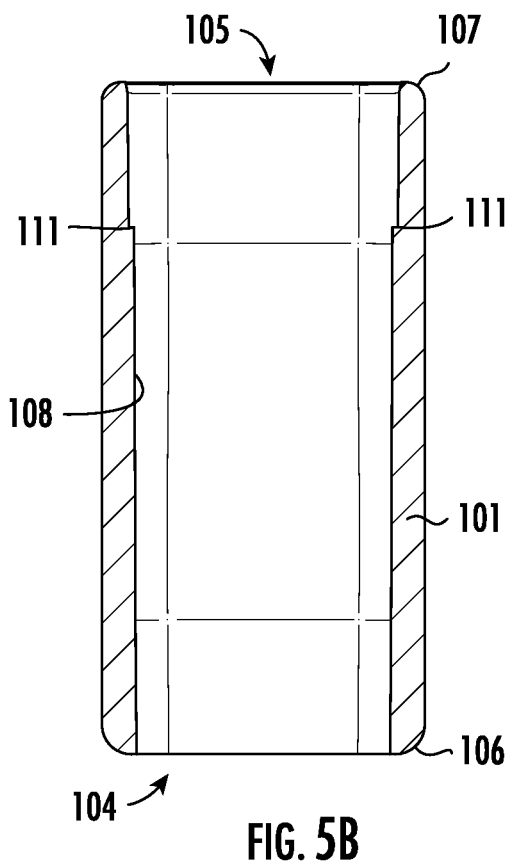
FIG. 5B is a vertical section of the outer tubular body of the fragrance diffuser shown in FIG. 4A, viewed from the front side thereof as shown in the drawing.
Figure 6A:
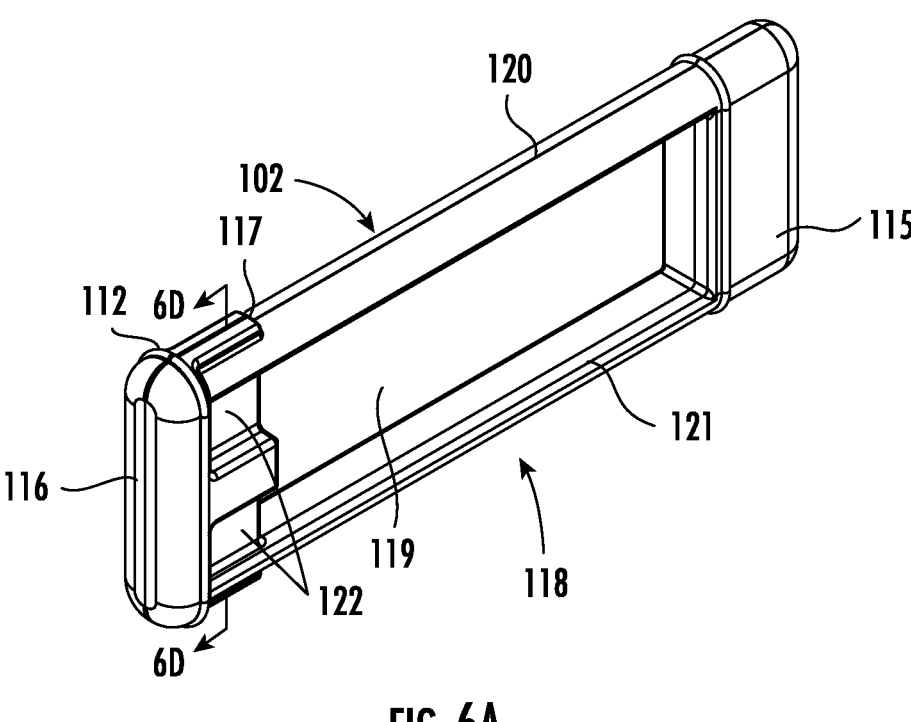
FIG. 6A is a perspective view of the inner piston member which is received within the outer tubular body of the fragrance diffuser shown in FIG. 4A.
Figure 6B:
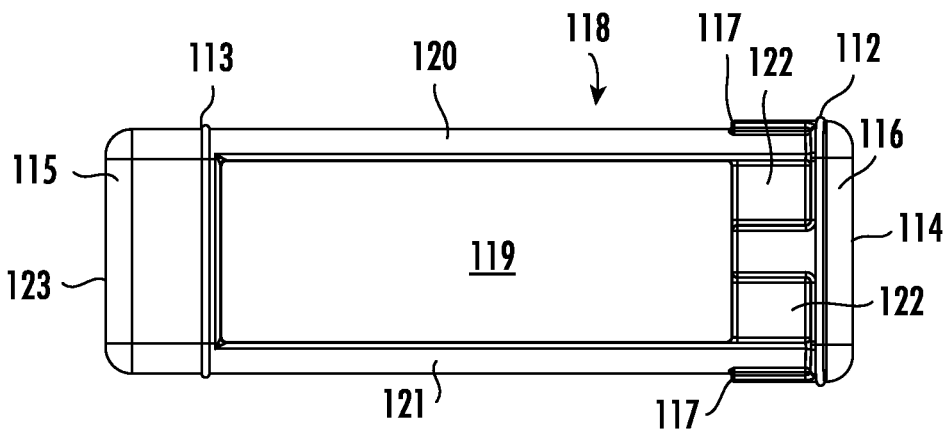
FIG. 6B is a front elevation view of the inner piston member shown in FIG. 6A.
Figure 6D:
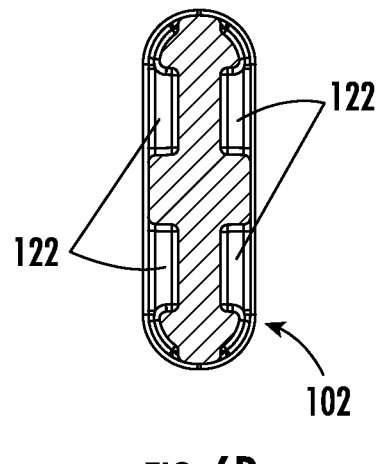
FIG. 6D is a cross section view of the inner piston member shown in FIG. 6A, taken along lines 6D-6D thereof.
Figure 6C:
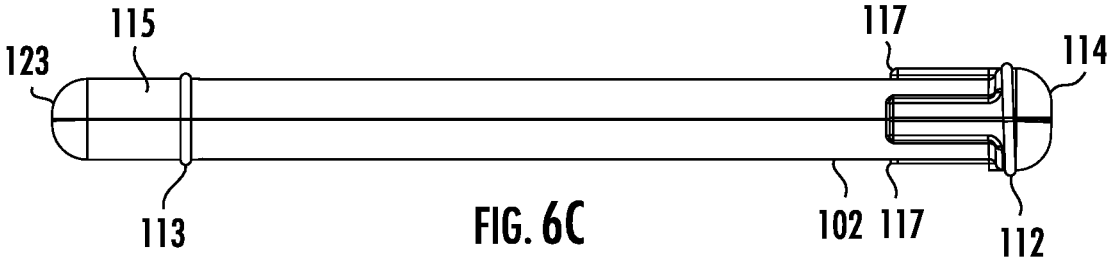
FIG. 6C is a side elevation view of the inner piston member shown in FIG. 6A.

Referring to FIGS. 5A and 5B, in the present embodiment, it can be seen that a gradual thickening of the walls of the outer tubular body 101 causes the inner chamber or passageway 108 extending therethrough to constrict or taper diametrically in size slightly from open end 107 to the opposite open end 106. This can be seen in both FIGS. 5A and 5B, where the wall thickness of body 101 is seen to be slightly greater adjacent open end 106 than open end 107, thus causing the transverse dimensions of passageway 108 to constrict slightly as it progresses through tubular body 101.

As further shown in FIGS. 4 and 5, the wall thickness of tubular member 101 immediately adjacent open end 107 is also thinner than the remaining section of the wall, thus creating a radially inward protruding shoulder 111. As will be discussed hereafter and shown in FIG. 4G, shoulder 111 creates a stop for piston 102 within chamber 108, which helps to facilitate proper sealed positioning of piston 102 when the fragrance diffuser is closed, and also prevents potential damage of piston 102 as a result of overtravel within body member 101.

With reference now being had to FIGS. 6A-6D of the drawings (hereinafter collectively "FIG. 6"), the construction for piston 102 is shown in greater detail. As seen, piston 102 is an elongated member having opposite end portions 115 and 116. As with the initial embodiment of FIGS. 1-3, for most effective and efficient operation of the present fragrance diffuser 100, it is contemplated that piston 102 be greater in length than the outer tubular body 101 within which it is carried. If so, at least one of the end portions 115 and 116 of the slidable piston 102 will be visibly exposed and readily accessible at all times to the user. Thus, the user may easily activate and deactivate the fragrance diffuser 100, and adjust the positioning of piston 102 within the tubular outer body 101, by merely pushing the piston 102 in one direction or the other with one's fingers.

As shown further in FIGS. 4 and 6, end portion 115 of piston 102 is constructed with a generally rectangular or oval cross-sectional shape and dimensions closely approximating, but slightly less than, that of opening 104 in the outer tubular body member 101. Accordingly, end portion 115 of piston 102, which is aligned during assembly with opening 104 in tubular body member 101, is permitted to move freely through opening 104 of body 101 upon axial pressure being applied to one of the opposite end portions 115 or 116 of piston 102.

The opposite end portion 116 of piston 102 is also compliantly sized and shaped to slide in and out of the opening 105 formed in end 107 of outer body 101. Since the opening 105 at end 107 of the tubular body 101 is slightly larger than the opening 104 at the opposite end opening 106, the terminal end portion 116 of piston 102 is also slightly larger than end portion 115. This helps to ensure that the piston member 102 is properly assembled and not inadvertently inserted backwards within the outer tubular body 101. Here again, the cross-sectional or diametrical dimensions of end portion 116 of piston 102 are sized just slightly less than that of the inner wall surface of passageway 108 adjacent open end 107, such that end portion 116 of piston 102 is permitted to move freely through opening 105 of body 101 upon axial pressure being applied to one of the opposite end portions 115 or 116 of piston 102.

Importantly, as shown in FIG. 6, piston 102 constricts diametrically slightly at a point axially inward from the distal end 114 thereof, thus forming opposing lips 117. Once assembled, lips 117 function as a stop or catch mechanism which engage shoulder 111 of the outer body 101 when the piston 102 is fully inserted to a closed position therein. As seen in FIG. 4G, when the fragrance diffuser is fully closed, shoulder 111 formed on the interior of tubular member 101 functions as a travel-stop limit for piston 102 to ensure that the piston is properly positioned in sealed relation to the outer tubular body 101. Shoulder 111 also helps to prevent damage to the piston 102 and possibly to the tubular body 101 due to overtravel of one member relative to the other.

As further shown in FIGS. 4 and 6, to perfect a seal of piston 102 against the inner wall surface of chamber 108 and control movement thereof within the outer body 101, the opposite end portions 115 and 116 of piston 102 are formed with radially outward protruding peripheral sealing members 112 and 113, respectively. In the present embodiment, as seen in FIG. 4E, sealing member 112 is located just axially inward from the distal end 114 of the piston 102 and is correspondingly sized to seal circumferentially against the interior wall surface of chamber 108 near opening 105. More specifically, sealing member 112 is comprised of at least one annular sealing lobe which extends circumferentially around the periphery of end portion 116, where it functions to bear against the interior wall surface of chamber 108 and help effect a proper seal thereagainst when the diffuser 100 is deactivated and closed.

Similarly, at least one sealing member 113 in the form of an annular sealing lobe extends about the periphery of the opposite end portion 115 of piston 102. As best shown in FIG. 4F, sealing member 113 is located axially inward from the distal end 123 of piston 102 a distance sufficient to ensure that end portion 115 of piston 102 remains sealed at all times through full movement of piston 102 within tubular body 101. Therefore, as piston 102 moves between an open/activated position with end portion 116 pulled outward from within tubular body 101 (FIG. 4D) and a fully closed/deactivated position with lips 117 of piston 2 engaging shoulder 111 of tubular body 101 (FIG. 4G), end portion 115 of piston 102 will always remain sealed against the inner surface of chamber 108.

Thus, upon full closure of the fragrance diffuser 100 (FIG. 4G), end portion 116 of piston 102 is guided within opening 105 of tubular body 101 to a position where the lips 117 of piston 102 are in engagement with the shoulder 111 of the outer tubular body 101. Once seated, sealing lobe 112 will bear firmly in sealing relation against the inner wall surface of chamber 108 of body 101. Consequently, by pressing the end portion 116 of piston 102 axially inward within the confines of the outer body 101, both end portions 115 and 116 of piston 102 are caused to seal against the inner wall surface of chamber 108, thus sealing the entire intermediate section 118 of piston 102 from exposure to the outer atmosphere of the surrounding environment.

As best shown in FIGS. 4 and 6, the intermediate section 118 of piston 102 is adapted to hold and support the fragrance carrier member 103. In the present embodiment, the intermediate section 118 of piston 102 includes an open pocket 119 formed by a framework of sides 120 and 121 extending between opposite end portions 115 and 116 of piston 102. The fragrance carrier 103 is shown in the drawings in the form of a small pad or wafer (FIG. 7), but many different configurations are conceivable without departing from the scope of the invention herein. Accordingly, the manner of retaining the fragrance carrier 103 within the confines of piston 102 may also vary without departing from the scope of the invention herein. Fragrance carrier member 103 can be constructed of any material capable of absorbing and passively emitting the fragrance of an essential oil or other scented oil/liquid with which it is impregnated. As noted previously, such known materials may include, without limitation, silicone, cotton, paper, wood, stone, ceramic, etc., or combinations thereof.

Figure 7:
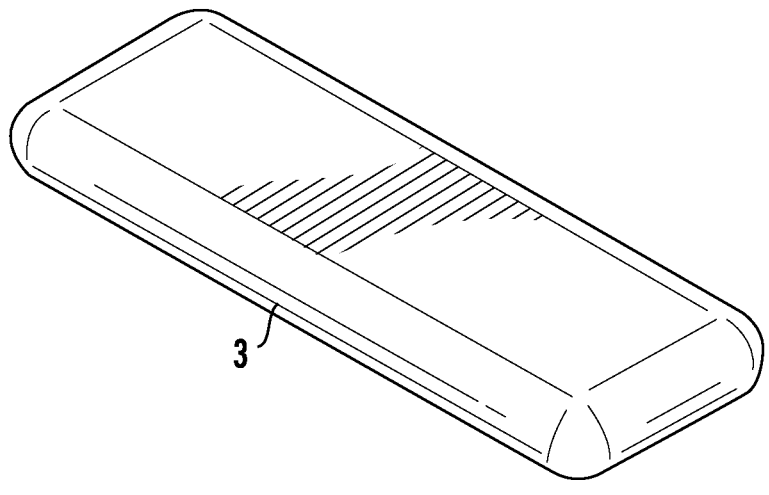
FIG. 7 is a perspective view of the fragrance carrier/diffusion member which is impregnated with a fragrance oil and carried by the inner slidable piston member of the fragrance diffuser shown in FIG. 4A.

As seen best in FIGS. 4 and 7, the fragrance carrier member 103 is configured with dimensions corresponding to the interior pocket 119 of piston 102, such that the fragrance carrier 103 is held in place by the surrounding framework, i.e., sides (120,121) and end portions (115,116). As shown best in FIG. 4C, fragrance carrier 103 is designed with a thickness corresponding to the surrounding framework of piston 102, and just slightly less than the corresponding cross-sectional dimension of chamber 108 in body member 101. This creates a minor clearance between fragrance carrier 103 and the inner wall surface of chamber 108 which accommodates for possible swelling of the fragrance carrier 103 when impregnated with a scent oil. Therefore, fragrance carrier 103 is designed to slide freely with piston 102 inside of tubular body 1 at all times without interference with the inner wall of tubular member 1.

Accordingly, the fragrance carrier member 103 is contained laterally between the intermediate section 118 of piston 102 and the inner wall surface of chamber 108 of outer body member 101. Axially, the fragrance carrier member 103 is held in place by end portions 115 and 116 of piston 102. As such, the fragrance carrier member 103 is effectively retained between opposing sealing members 112 and 113 formed in piston 102 and the outer body 101 of the diffuser 100. Thus, when the fragrance diffuser is closed, the fragrance carrier member 103 is sealed atmospherically inside body member 101 from the outside environment.

As shown best in FIG. 6, at the juncture between end portion 116 and intermediate section 118 of piston 102, at least a portion of the circumference of end portion 116 includes a plurality of axially extending open channels 122 which extend toward the open pocket area 119 that is formed by the intermediate section 118 of piston 102. As seen best in FIG. 4, when the fragrance diffuser 100 is assembled, these channels 122 fluidly communicate with the open area 119 within which the fragrance carrier member 103 is contained and carried by the intermediate section 118 of piston 102.

Figure 4A:
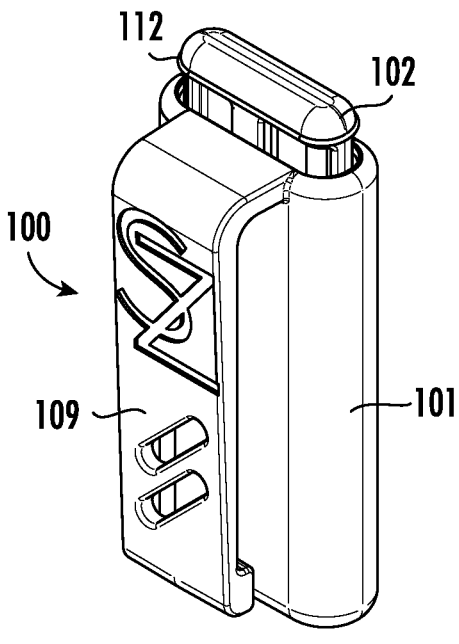
FIG. 4A is a perspective view of an alternative embodiment of our new passive emission fragrance diffuser, showing the diffuser in its assembled open position.
Figure 4B:
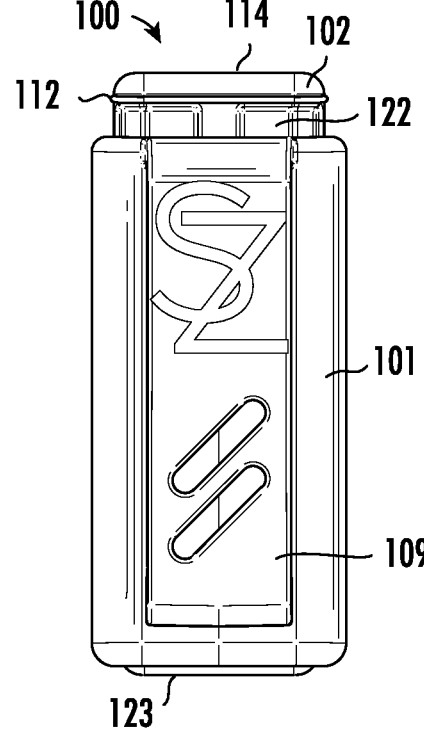
FIG. 4B is a front elevation view of the fragrance diffuser shown in FIG. 4A, shown in its open position.
Figure 4C:
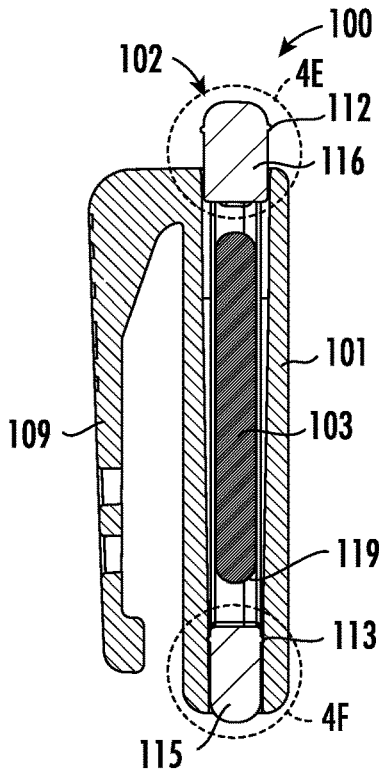
FIG. 4C is a vertical section view of the fragrance diffuser shown in FIG. 4A, viewed in its open position from the left side thereof as shown in the drawing.
Figure 4D:
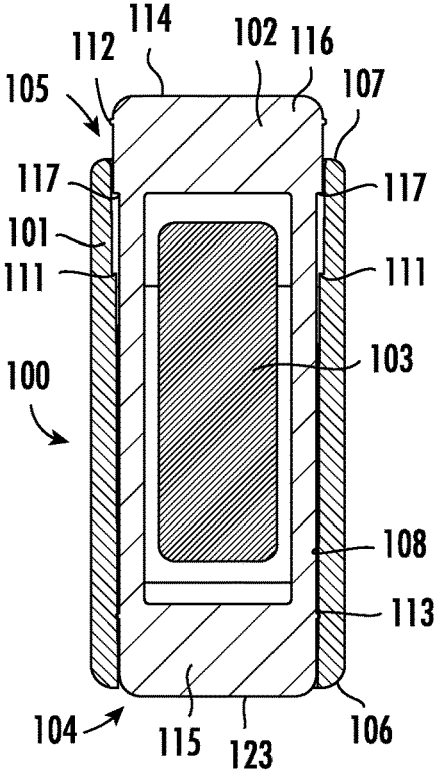
FIG. 4D is a vertical section of the fragrance diffuser shown in FIG. 4A, viewed in its open position from the front side thereof as shown in the drawing.
Figure 4E:
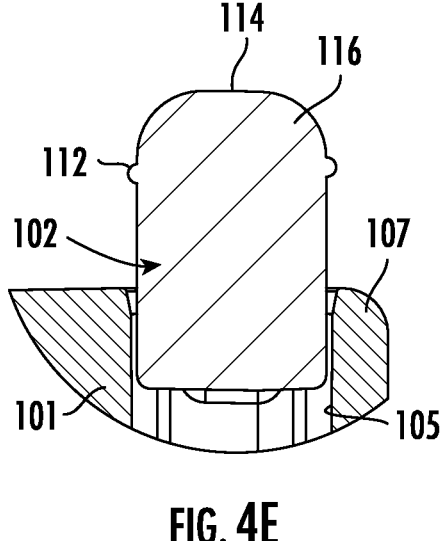
FIG. 4E is a detailed close-up view of one end of the fragrance diffuser in its open position, as shown and labeled in FIG. 4C.
Figure 4F:
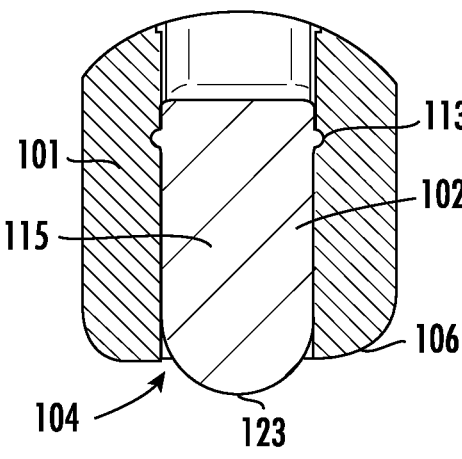
FIG. 4F is a close-up detailed view of the opposite end of the fragrance diffuser in its open position, as shown and labeled in FIG. 4C.
Figure 4G:
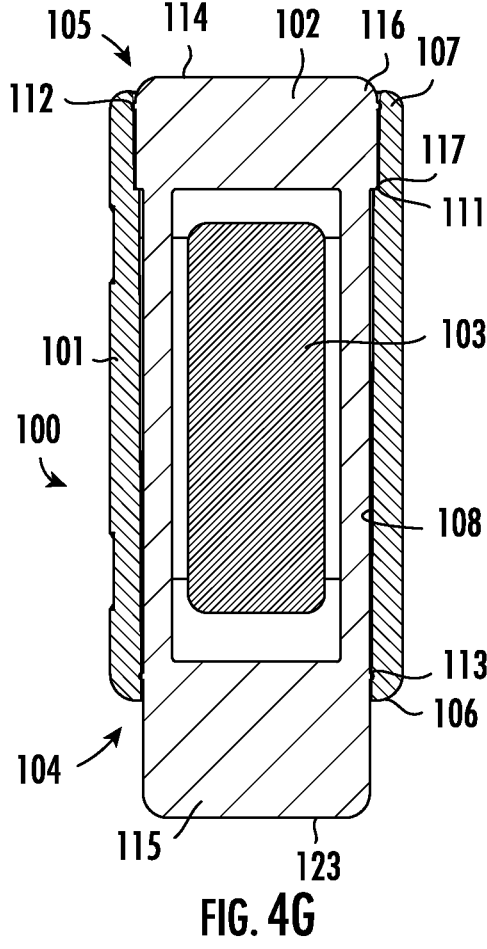
FIG. 4G is a vertical section view of the fragrance diffuser shown in FIG. 4A, viewed from the front side thereof in its closed position.

Accordingly, as shown in FIG. 4B, activation of the fragrance diffuser may be accomplished by simply applying inward axial pressure upon end 123 of piston 102, thus causing piston 102 to slide axially (upward in drawing) within outer body 101. Such movement has the effect of breaking the seal (at member 112) between end portion 116 of piston 102 and the outer tubular body 101. When such seal is broken, the fragrance from the diffuser 100 is permitted to flow passively from the contained space 119 within outer body 101, through channels 122 formed in end portion 116 of piston 102, and out to the surrounding atmosphere. Depending on how far inward end portion 115 of piston 102 is moved dictates how much of the axially extending channels 122 will be exposed to the atmosphere, and consequently how much fragrance is emitted to the surrounding environment. Thus, the amount and strength of the scent emitted by the fragrance diffuser may be effectively controlled through adjustment of the positioning of piston 102 within the outer body 101. When the end 115 of piston 102 is pressed axially inward to a position substantially flush with the end 106 of outer body 101 (FIGS. 4A-4D), the fragrance diffuser is constructed to be near or fully open with channels 122 having maximum exposure to the surrounding atmosphere.

The section of end portion 116 with channels 122 also creates a barrier between the fragrance carrier material 103 and the outside environment. Therefore, there is no direct contact between the fragrance carrier material 103 and the skin/clothing of the person wearing the fragrance diffuser 100, or other article to which the fragrance diffuser 100 is clipped. One can safely open and close the diffuser 100 without concern of coming in direct contact with the fragrant oil. This allows the fragrance diffuser 100 to be clipped virtually anywhere desired, either visibly on the exterior of a clothing article or on the inside, out of sight. By securing the fragrance diffuser to the inside on a person's clothing article, the body temperature of an individual can actually help heat the silicone/material of the fragrance carrier 103 and increase emission/evaporation of the scented oil, thus enhancing the release of fragrance.

It is noteworthy that the foregoing discussion describes the fragrance carrier member 103 as being carried by the piston 102 in movable relation to the outer body 101 of the fragrance diffuser 100. However, it is certainly conceivable that the fragrance carrier member 103 could be retained by the outer body member 101 in a stationary position relative to the sliding tubular member 102, without departing from the scope of the invention herein. In either case, movement of the slidable piston 102 in one direction or the other will effectively open or close the sealed ends of diffuser 100, thereby allowing emission of the fragrance through channels 122 to the surrounding atmosphere or sealing the same therefrom.

The fragrance carrier material 103 can be either prescented and used as a throwaway item, if desired, or it is contemplated that additional fragrant oil can be added to the fragrance carrier material 103 through the vented channel openings 122 formed on the end portion 116 of piston 102. Since piston 102 is readily removable from the outer body 101 of the diffuser 100, it is also possible to form the fragrance carrier 103 as a replaceable item, such that the fragrance diffuser 100 is reusable. Still further, the fragrance carrier 103 could be sold separately from the fragrance oil, thus allowing the user to self-infuse the fragrance carrier 103 prior to use with any of a variety of different fragrance oils, as desired.

To close and deactivate the fragrance diffuser, axial pressure may simply be applied to end 114 of piston 102, thus causing movement of piston 102 back toward its closed position, shown in FIG. 4G. As piston 102 progresses in this direction, channels 122 formed in end portion 116 of piston 102 become less exposed to the ambient air of the surrounding environment, and the fragrance begins to dissipate. Upon reaching full closure, i.e., where lips 117 of piston 102 seat against shoulder 111 of tubular body 101, both end seals 112 and 113 of piston 102 are perfected, thus closing off all fragrance from the surrounding environment.

Accordingly, the location of lips 117 on piston 102 and the shoulder 111 of tubular body 101 are determined and preset by design such that, upon closure of the fragrance diffuser, both end portions 115 and 116 of piston 102 are sealed against the out tubular body 101 and over-travel of the piston 102 is prevented. This prevents the fragrance carrier member 103 contained within body 101 from emitting any gases into the surrounding environment upon closure of the device.

Figure 8:
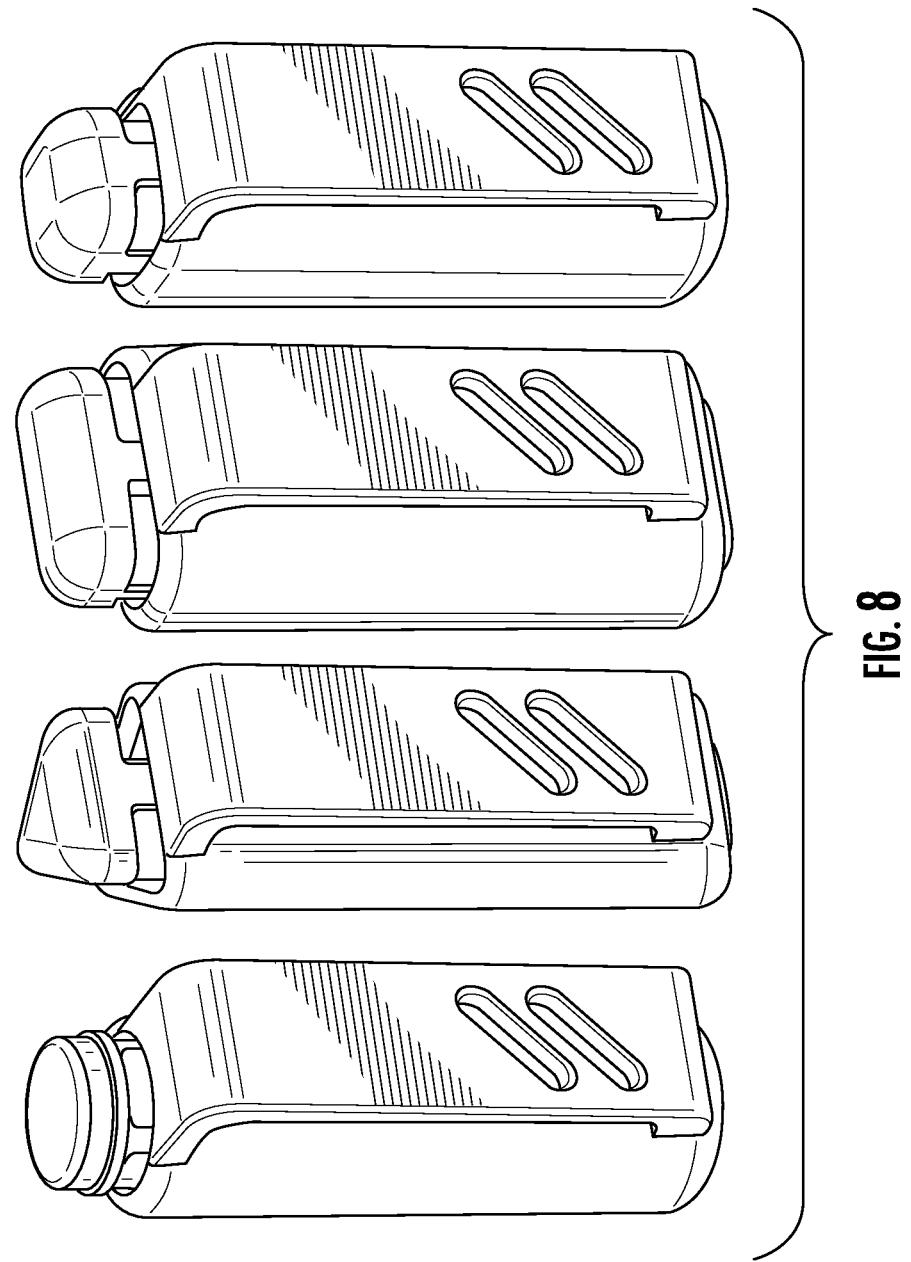
FIG. 8 is a perspective drawing depicting, without limitation, various different shapes of fragrance diffusers incorporating the principles of our invention.

With reference now being made to FIG. 8, it can be seen that a number of potential design configurations incorporating the principles of our invention are possible. Without limiting the scope of the invention herein, it can be seen that, in addition to a fragrance diffuser having a circular or rectangular/oval cross section configuration, as discussed above, diffusers with generally triangular and square cross sections are also conceivable.

Given the simplicity of the foregoing fragrance diffuser design, it is contemplated that the diffuser assembly may be constructed as a slow-emitting, low-cost, throw-away device which can be disposed of after the fragrance carrier member (3,103) becomes fully dissipated and ceases to emit the desired aroma. On the other hand, it is also readily conceivable the compartment or area (19,119) defined by the intermediate section (18,118) of piston (2,102) could be made accessible for insertion of a new replacement fragrance carrier member (3,103), or be constructed as a re-fillable chamber capable of being refilled with any desired fragrance oil or essential oil of the user's choice. Still further, the fragrance carrier (3,103) could be sold separately from the fragrance oil, thus allowing the user to self-infuse the fragrance carrier (3,103) prior to use with any of a variety of different fragrance oils, as desired. Regardless of the manner in which the above fragrance diffuser is used, the simplicity and compact nature of its design renders the device suitable for use as a long-lasting, passive, fragrance diffuser which is highly versatile for personal use in a multiplicity of circumstances and different environments, and which may be readily activated and deactivated with ease, as desired.

Certain terminology is used herein for purposes of reference only, and thus is not intended to be limiting. For example, terms such as "upper", "lower", "above", "below", "top", "bottom", "upward", "downward", "rearward", and "forward" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The disclosure herein is intended to be merely exemplary in nature and, thus, variations that do not depart from the gist of the disclosure are intended to be within the scope of the disclosure. Such variations are not to be regarded as a departure from the spirit and scope of the disclosure, which comprises the matter shown and described herein, and set forth in the appended claims.

The invention claimed is:

1. A passive emission fragrance diffuser for personal use, comprising:
    (a) an outer tubular body having opposite first and second open ends and an axis extending therebetween;
    (b) a piston member telescopically received within said tubular body, said piston member being longer than said tubular body and slidable therewithin;
    (c) a first fluid seal being integrally formed with said piston member between said piston member and said tubular body adjacent said first open end;
    (d) a second fluid seal being integrally formed with said piston member between said piston member and said tubular body adjacent said second open end;
    (e) a fragrance carrier member being retained within said tubular body between said first and second fluid seals; and
    (f) said first fluid seal being releasable upon selective movement of said piston member within said tubular body, thereby permitting passive emission of the fragrance from said fragrance carrier member to ambient air outside said tubular body.

2. The passive emission fragrance diffuser set forth in claim 1, wherein said first fluid seal is releasable upon selective axial movement of said piston member in one direction and resealable upon selective axial movement of said piston in the opposite direction.

3. The passive emission fragrance diffuser set forth in claim 1, wherein said piston member includes a plurality of circumferentially spaced channels extending between said first fluid seal and said fragrance carrier member.

4. The passive emission fragrance diffuser set forth in claim 1, wherein said fragrance carrier member is retained within a cavity formed in said piston member and is movable therewith within said tubular body.

5. The passive emission fragrance diffuser set forth in claim 1, wherein said piston member is movable within said tubular body between an open position where said first fluid seal is released and a closed position where said first and said second fluid seals are both fluidly sealed.

6. The passive emission fragrance diffuser set forth in claim 5, wherein said tubular body includes an interior stop for limiting further movement of said piston member upon reaching said closed position.

7. The passive emission fragrance diffuser set forth in claim 5, wherein said piston member protrudes slightly outward from said first open end of said tubular body when in said open position and protrudes slightly outward from said second open end of said tubular body when in said closed position.

8. The passive emission fragrance diffuser set forth in claim 1, wherein said tubular body includes an exterior clip for securing the fragrance diffuser to a person's clothing or personal article.

9. The passive emission fragrance diffuser set forth in claim 1, wherein said fragrance carrier member is comprised of an absorptive material impregnated with a fragrant oil.

10. A passive emission fragrance diffuser for personal use, comprising:
    (a) an outer tubular body having a length and opposite first and second open ends;
    (b) a piston member positioned within said tubular body and being moveable therein along an axis extending between said first and second open ends, said piston member being longer than said tubular body;
    (c) a first circumferential seal being integrally formed with said piston member adjacent a first piston end and a second circumferential seal being integrally formed with said piston member adjacent a second piston end, wherein the distance between said first circumferential seal and said second circumferential seal is less than said length of said tubular body;
    (d) said piston member being moveable within said tubular body between a closed position where said first circumferential seal and said second circumferential seal engage and fluidly seal against an inner surface of said tubular body, and an open position where said first circumferential seal breaks engagement with said inner surface of said tubular body and releases its fluid seal thereagainst; and
    (e) a fragrance carrier member being retained by said piston member between said first circumferential seal and said second circumferential seal, such that when said piston member is in said closed position, the fragrance from said fragrance carrier member is sealed within said tubular body, and when said piston member is in said open position, the fragrance from said fragrance carrier member is exposed to ambient air outside said tubular body and allowed to passively emit its fragrance thereto.

11. The passive emission fragrance diffuser set forth in claim 10, wherein at least a portion of said piston member adjacent said first piston end is shaped to closely fit said inner surface of said tubular body, said portion including a plurality of circumferentially spaced channels extending axially from said first circumferential seal toward said fragrance carrier member.

12. The passive emission fragrance diffuser set forth claim 11, wherein said channels connect said first circumferential seal to said fragrance carrier member and adjustment of the position of said piston member within said tubular body causes adjustable selective exposure of said channels to ambient air outside of said tubular body.

13. The passive emission fragrance diffuser set forth in claim 10, wherein said fragrance carrier member is comprised of an absorptive material impregnated with a fragrant oil.

14. The passive emission fragrance diffuser set forth in claim 10, wherein said tubular body includes an interior stop for limiting further movement of said piston member upon reaching said closed position.

15. The passive emission fragrance diffuser set forth in claim 10, wherein said piston member protrudes slightly outward from said first open end of said tubular body when in said open position and protrudes slightly outward from said second open end of said tubular body when in said closed position.

16. The passive emission fragrance diffuser set forth in claim 10, wherein said tubular body includes an exterior clip for securing the fragrance diffuser to a person's clothing or personal article.

17. A method of selectively delivering a passive fragrance emission from a fragrance diffuser to a surrounding environment, comprising the steps of:

(a) providing an outer tubular body having a length and opposite first and second open ends with an axis extending therebetween;

(b) providing a piston member for telescopic insertion within said tubular body which is longer than said tubular body, said piston member being slidable within said tubular body and having a first circumferential fluid seal formed integrally therewith between said piston member and said tubular body adjacent a first piston end and a second circumferential fluid seal formed integrally therewith between said piston member and said tubular body adjacent a second piston end, wherein the distance between said first circumferential fluid seal and said second circumferential fluid seal is less than said length of said tubular body;

(c) providing a fragrance carrier member to be retained within said tubular body between said first circumferential fluid seal and said second circumferential fluid seal of said piston member;

(d) inserting said piston member and said fragrance carrier member within said tubular body through one of said first and said second open ends thereof, with said fragrance carrier member positioned between said first circumferential fluid seal and said second circumferential fluid seal of said piston member, and with said first circumferential fluid seal and said second circumferential fluid seal of said piston member in fluidly sealed engagement against an inner surface of said tubular body; and (e) selectively pressing on said second piston end to move said piston member axially within said tubular body to an open position which releases said first circumferential fluid seal between said piston member and said tubular body, thus allowing passive emission of the fragrance from said fragrance carrier member to the ambient air surrounding the fragrance diffuser.

18. The method set forth in claim 17, including the step of selectively pressing on said first piston end to move said piston member axially within said tubular body to a closed position which reseals said first circumferential fluid seal of said piston member against said inner surface of said tubular body, thus closing off and preventing further emission of the fragrance from said fragrance carrier member to the ambient air surrounding the fragrance diffuser.

19. The method set forth in claim 18, including the step of providing said tubular body with an interior stop for limiting further movement of said piston member upon reaching said closed position.

20. The method of claim 17, including the step of providing said piston member with a plurality of circumferentially spaced channels extending between said first circumferential fluid seal and said fragrance carrier member.

\* \* \* \* \*